United States Patent [19]

Pellaux et al.

[11] Patent Number: 5,616,826
[45] Date of Patent: Apr. 1, 1997

[54] PHOTOACOUSTIC ANALYZER AND METHOD

[75] Inventors: Jean-Paul Pellaux; John M. Hale, both of Geneva; Ion Bals, Caran, all of Switzerland

[73] Assignee: Orbisphere Laboratories Neuchâtel SA, Neuchâtel, Switzerland

[21] Appl. No.: 443,533

[22] Filed: May 18, 1995

[30] Foreign Application Priority Data

Jun. 4, 1994 [EP] European Pat. Off. ............. 94810332

[51] Int. Cl.$^6$ ......................................................... G01N 21/17
[52] U.S. Cl. ...................... 73/24.02; 250/343; 356/437; 356/432
[58] Field of Search ............................... 73/24.02, 24.01; 250/343, 351; 356/432, 437

[56] References Cited

U.S. PATENT DOCUMENTS

| Re. 31,879 | 5/1985 | Lübbers et al. . | |
|---|---|---|---|
| 2,106,612 | 1/1938 | Pierre et al. | 250/548 X |
| 3,820,901 | 6/1974 | Kreuzer . | |
| 3,938,365 | 2/1976 | Dewey, Jr. | 73/24.02 |
| 3,948,345 | 4/1976 | Rosencwaig | 73/659 X |
| 4,027,972 | 6/1977 | Davies | 250/343 X |
| 4,163,382 | 8/1979 | Amer | 73/24.02 |
| 4,594,004 | 6/1986 | Ishida et al. | 73/24.02 X |
| 4,622,845 | 11/1986 | Ryan et al. | 73/24.02 |
| 4,817,413 | 4/1989 | Asano et al. . | |
| 4,818,882 | 4/1989 | Nexo et al. . | |
| 4,980,278 | 12/1990 | Yamada et al. . | |
| 5,003,488 | 3/1991 | Hardy | 356/440 X |
| 5,030,420 | 7/1991 | Bacon et al. . | |

FOREIGN PATENT DOCUMENTS

| 0231639 | 8/1987 | European Pat. Off. . | |
|---|---|---|---|
| 0433385 | 3/1990 | European Pat. Off. . | |
| 4034375 | 4/1992 | Germany | 73/24.02 |
| 94027 | 5/1984 | Japan . | |
| 116724 | 5/1956 | U.S.S.R. | 73/24.01 |
| 449286 | 2/1974 | U.S.S.R. | 73/24.01 |
| 2059574 | 4/1981 | United Kingdom | 356/435 |

OTHER PUBLICATIONS

"A Toxic Gas Monitor with ppb Sensitivity Using on Automated Laser Optoacoustic Spectrometer", Laser & Elektro–Optik, vol. 11, No. 2, 1979 pp. 18–19.
Kreuzer et al. "Air Pollution: Sensitive Detection of Ten Pollutant Gases by Carbon Monoxide and Carbon Dioxide Lasers", Science vol. 177, 28 Jul. 1972, pp. 347–349.
Analytical Chemistry, vol. 54, No. 9, pp. 1484–1489 dated Aug., 1982. Poizat et al, "Determination of Nitrogen Dioxide by Visible Photoacoustic Spectroscopy."

Primary Examiner—Hezron E. Williams
Assistant Examiner—Daniel S. Larkin
Attorney, Agent, or Firm—Wigman, Cohen, Leitner & Myers, P.C.

[57] ABSTRACT

A photoacoustic device for analysis of fluids. The device is made up of (A) a source of a pulsating beam of light, preferably of the chopper type, and (B) an enclosure, preferably an elongated structure having a generally cylindrical, e.g. essentially tubular shape; and containing and holding—in sonic insulation—at least one reference chamber and at least one measuring chamber in an essentially linear or serial arrangement in a common cell within the enclosure, preferably in an essentially coaxial arrangement; the enclosure and the common cell provide a path P for the pulsating beam of light through the reference chamber and through the measuring chamber. For most purposes, it is preferred that the light beam pass first through the reference chamber and subsequently into the measuring chamber. Optionally, a second reference chamber is arranged at the end of the measuring chamber and a second measuring chamber may follow.

5 Claims, 4 Drawing Sheets

PHOTOACOUSTIC ANALYZER AND METHOD

BACKGROUND OF THE INVENTION

1. Field of the Invention

This invention generally relates to the art of analyzing fluids and specifically to photoacoustic devices and methods for quantitative analysis of fluids, normally in a gaseous state.

2. Prior Art

Various analytic devices and methods using photoacoustic techniques are known in the art, e.g. as disclosed in U.S. Pat. Nos. 3,820,901, 3,938,365, 3,948,345, 4,163,382, 4,818,882, EP-A-0 231 639, EP-A-0 433 385 all of which are incorporated herein by way of reference for all purposes.

The principle that is common to photoacoustic devices and methods is interaction of light, generally in the infrared portion of the electromagnetic spectrum, with a gaseous sample containing a known analytic species of interest—which may but need not be an impurity—in an unknown concentration for generating a sonic signal dependent upon the concentration of the species of interest.

Research by applicant leading to the present invention has indicated that a major problem with many types of prior art photoacoustic devices is poor reproducibility of results, notably if unstable substances, such as ozone ($O_3$), are the species of interest.

OBJECTS AND SUMMARY OF THE INVENTION

Thus, a first general object of the invention is an improvement of reproducibility of the results of optoacoustic devices and methods, notably when analysing chemically unstable substances, such as ozone.

According to the invention, an analytic species of interest is considered "unstable" if it will or may decompose under the conditions of measurement. Conversely, an analytic species of interest is considered to be "stable" if it does not decompose to a significant degree under the conditions of measurement.

Even with relatively stable analytical species of interest that are presumed to be inherently suitable for photoacoustic methods ($NH_3$, $CO_2$, $H_2O$, $CO$, $NO_x$, $SO_x$ and various organic substances such as ethylene) problems of sensitivity and reproducibility have been observed, notably when such species were present in relatively high concentrations, e.g. in the range of from 5 to 50% by volume or higher. Also, many prior art devices tend to have a relatively complicated structure and/or require special skill on the side of the operator.

Accordingly, it is another main object of the present invention to provide for a photoacoustic device and method that diminishes or eliminates the above-mentioned disadvantages of the prior art.

This object is achieved according to a first general embodiment by a photoacoustic device for analysis of fluids comprising:

(A) a source of a pulsating beam of light, e.g. as exemplified hereinbelow;

(B) an enclosure, preferably an elongated structure having a generally cylindrical, e.g. essentially tubular shape, and containing and holding—in sonic insulation—at least one reference chamber and at least one measuring chamber in an essentially linear or serial arrangement in a common cell within the enclosure means, preferably in an essentially coaxial arrangement; the enclosure means and the common cell provide a path for the pulsating beam of light through the reference chamber and through the measuring chamber. For most purposes it is preferred that the light beam passes first through the, or a first, reference chamber and subsequently into the measuring chamber. Optionally, a second reference chamber is arranged at the end of the measuring chamber and a second measuring chamber may follow. Theoretically, there is no limit to the number of reference chambers and measuring chambers in alternating arrangements but the use of one or two reference chambers with a subsequent or intermediate measuring chamber is preferred for many purposes.

The measuring chamber or chambers has (have) inlet and outlet means or ports, such as conduits and valves, for passing a gaseous medium containing the known species of interest in an unknown concentration into and out of the measuring chamber; the reference chamber(s) and the measuring chamber(s) each contain a sound detector, such as a microphone or other transducer capable of converting sound within the frequency range generated by the pulsating beam, into an electric signal in relation to the sound. The reference chamber(s) contain(s) a gaseous medium suitable for serving as a photoacoustic reference for the gaseous medium containing the species of interest.

If the species of interest is "stable" (no significant decomposition under the conditions of measurement) the gaseous medium in the reference chamber preferably contains the same constituents as the gaseous medium in the measuring chamber. With chemically unstable substances, such as ozone, as the species of interest the reference chamber preferably contains an essentially stable or inert gaseous medium that is suitable as a photoacoustic reference; such suitability or compatibility for use as a reference is understood in the photoacoustic art and is based upon similarity or compatibility of absorption, e.g. similar absorption in the same infrared frequency band. For example, various and normally gaseous organic substances, such as alkanes, e.g. propane, are suitable for use in the reference chamber when ozone is the species of interest.

Conventional electronic signal processors can be used to amplify and/or convert the output signal of the sound detectors or microphones into the desired units of measurement, e.g. parts per million, percents, weight units per volume, units of partial pressure, or the like. A part or all of the electronic signal processing means could be integrated into the analyzer according to the invention but this is not generally preferred because one and the same processor can be used in combination with a number of analytic devices for use in detecting specific species of interest and, hence, including different gaseous media in the reference chamber(s).

According to a second embodiment, the invention provides a photoacoustic analyzing method comprising the steps of:

(a) passing a pulsating beam of light having a predetermined frequency in an infrared frequency portion through an analytic device, preferably one according to the invention as defined above; generally, the analytic device comprises at least one reference chamber containing a gaseous reference medium and at least one measuring chamber containing a gaseous analysis medium so that the pulsating beam of light generates sound within the reference chamber and within the measuring chamber; the gaseous analysis medium contains a species of interest in an unknown concentration, and the gaseous reference consists of a medium capable of serving as a photoacoustic reference for said gaseous analysis medium as explained above;

(b) the sounds generated in the at least one reference chamber and in the at least one measuring chamber are detected separately, e.g. by a sound detector, such as a microphone, to generate a first and a second signal in relation to the sound generated in the reference chamber and in the measuring chamber; and (c) the first and the second signal are evaluated in relation with the unknown concentration of the species of interest, e.g. in a manner known per se in the art of electronic evaluation of analytical signals.

When analyzing samples that contain ozone or another unstable species of interest, the present invention provides for a novel calibration method in that the rate of decay of the chemically reactive substance is used for calibration of said analytic device. Such rate of decay can be determined under laboratory conditions for a given configuration of the device according to the invention and used under field conditions for calibrating the instrument.

BRIEF DESCRIPTION OF THE DRAWINGS

The invention will now be illustrated by way of example with reference to the enclosed drawings in which.

DETAILED DESCRIPTION OF THE PREFERRED EMBODIMENTS

Figure 1:
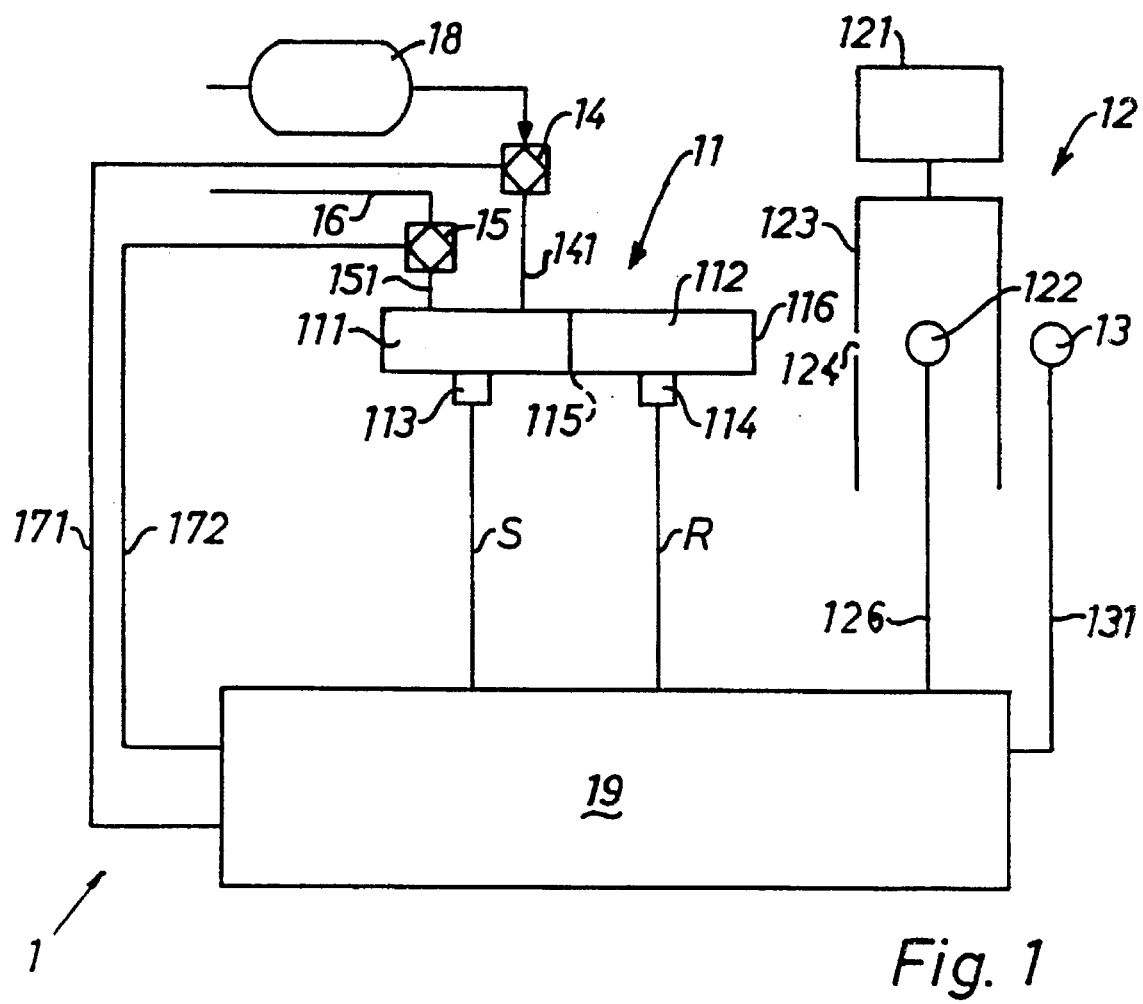
FIG. 1 is a diagrammatic view of an analytic system including a photoacoustic device according to the invention.

The analytic system 1 shown diagrammatically in FIG. 1 comprises a cell 11 having a measuring chamber 111 and a reference chamber 112 in linear or serial arrangement according to the invention. A source 12 of a pulsating, i.e. modulated, beam of light comprises a light source 122, e.g. an incandescent lamp or another emitter of electromagnetic radiation in the infrared region typically in the range of from about $3 \cdot 10^{11}$ to about $3.8 \cdot 10^{14}$ Hz. A filter (not shown in FIG. 1) may be used to select a specific range dependent in a manner known per se upon the gaseous medium under consideration. Generally, a frequency band having a high efficiency of transfer of light energy into thermal energy for the specific gaseous medium will be selected in a manner known per se in the photoacoustic art. An optional photodetector 13 may be provided for synchronization purposes and/or for monitoring the pulse frequency, and a power supply line 126 for light source 122 as well as a signal line 131 of detector 13 will be provided for operation.

A bell 123, e.g. of an essentially tubular configuration, having at least one perforation or opening 124 is connected to a drive 121, e.g. an electric motor. As the perforated bell 123 rotates with a predetermined and essentially constant rotational speed, e.g. 600 rpm, a modulated beam of light pulsating at a predetermined rate, e.g. 10 Hz, will be produced by the emitter or source 12.

The pulsating beam passes through an optional filter (not shown in FIG. 1) through a window 116 into reference chamber 112 and through a second window 115 into measuring chamber 111. Cell 11 is arranged within an enclosure (not shown in FIG. 1) in a manner explained in more detail below. Windows 115, 116 are made of a material that permits passage of infrared radiation. Such materials (also termed electroacoustic substrates) are known in the art, e.g. as referenced above, and include such substances as zinc selenide, gallium arsenide, and germanium.

Each chamber 111 and 112 is provided with a sound detector 113, 114, e.g. microphones. These detectors can be in physical contact with the cell but should not normally be in such contact with the enclosure; accordingly, a sonic shielding (not shown in FIG. 1) can be used for external sonic protection of the detectors 113, 114.

Measuring chamber 111 is connected with an inlet conduit 141 that can be opened and closed by a valve 14 which is connected with a source of the gas containing the analytic species of interest, optionally via pump 18. Chamber 111 is also connected with an outlet conduit 151 with associated valve 15 and a venting line 16. Preferably, both valves are automated valves for control via lines 171, 172.

Upon operation of system 1, the output signal S of detector 113 as well as the reference signal R are fed into a conventional signal processing and control unit 19; such units are available commercially, e.g. under the trade name MOCA, analyzer model 3610, from Orbisphere Laboratories, Neuchâtel, Switzerland.

Figure 2:
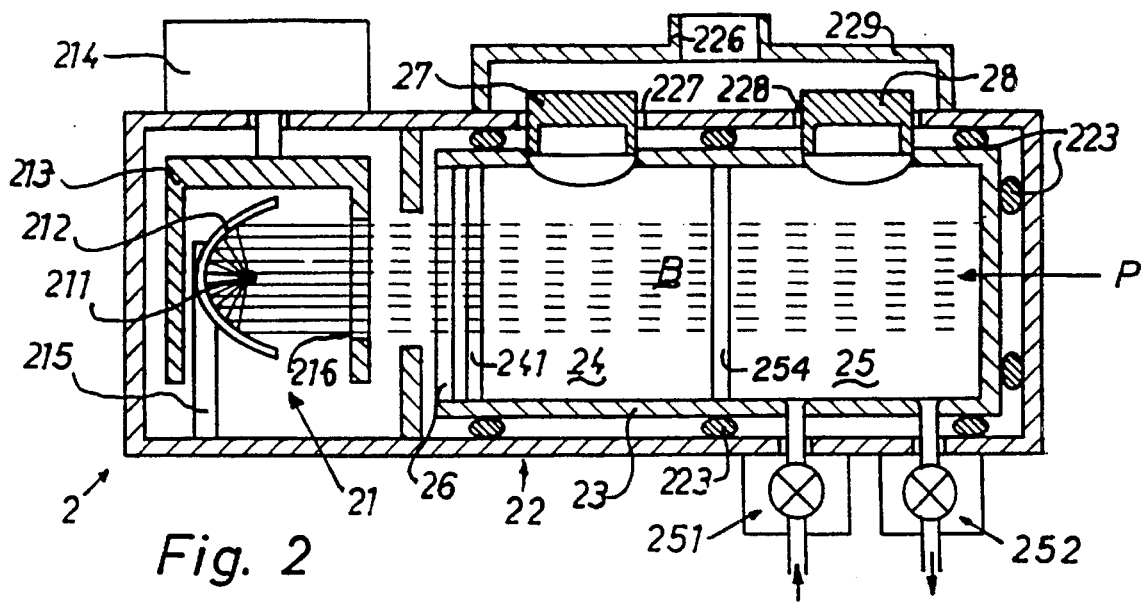
FIG. 2 is a diagrammatic sectional view of a preferred embodiment of the photoacoustic device according to the invention.

FIG. 2 is a semi-diagrammatic sectional view of a preferred embodiment of a photoacoustic device 2 according to the invention. It comprises a source 21 of a pulsating beam B of light emanating from an emitter 211, e.g. an incandescent lamp combined with a paraboloid reflector 212 or other paralleling means supported by bracket 215, within enclosure means 22. A rotatable bell 213 provided with an opening 216 is connected to motor 214 and is operated in the manner explained above in connection with FIG. 1. Generally, source 21 should be capable of providing a black-body spectrum. A detector (not shown in FIG. 2) can be used for monitoring and/or synchronization purposes as explained above.

Enclosure means 22 serves to integrally connect source 21 of the pulsating beam with measuring cell 23. A number of sonic insulators 223, e.g. cushions, sonic blocks or O-rings made of an elastomeric polymer serve to hold cell 23 suspended within enclosure 22, preferably in an essentially coaxial manner with regard to the longitudinal axis of enclosure 22 for simplicity of construction.

Preferably, enclosure 22 is of relatively heavy construction, e.g. with a wall thickness in the range of from about 5–15 mm, and is made of a relatively "heavy" (i.e. having the capacity of absorbing sonic energy) structural material, such as stainless steel. Cell 23, on the other hand, does not need heavy walling and can be made of a light structural metal, such as aluminum, an optionally reinforced synthetic polymer composition or the like.

An optional filter 26 is provided at the beam entrance end of reference chamber 24 and is made of a material that is selectively transparent to the infrared radiation selected for the particular device 2 considering the nature of the gaseous media within chambers 24 and 25. Selection of a proper filter is known in the photoacoustic art. Preferably, windows 241 near the entrance end of chamber 24 as well as window 254 between chambers 24 and 25 are made of a material that is transparent for infrared radiation but need not be selective.

The backside end of measuring chamber 25 can be provided with a mirror (not shown in FIG. 2) for infrared radiation. Inlet 251 including a valve and outlet 252, also including a valve, are provided for supplying measuring chamber 25 with a gaseous medium containing the (known) species of interest in an unknown concentration.

Sonic detectors 27, 28, e.g. microphones of the type known for use in photoacoustics, are provided to detect sonic frequencies produced by the gaseous media in chambers 24, 25 upon the impact of pulsating beam B and the thermal excitation of the gaseous media, or their constituents of interest, produced thereby. Signal lines (not shown in FIG. 2) are provided for connection with a signal processing device as explained above. As will be apparent from FIG. 2, enclosure 22 constitutes an integral device which provides a path P for beam B through reference chamber 24 and measuring chamber 25.

As is also apparent from FIG. 2, sonic detectors 27, 28 are connected with cell 23 but do not mechanically contact enclosure 22 because of openings 227 and 228 provided in enclosure 22. A sonic shield 229 is provided for acoustic protection of detectors 27, 28 against external noise and can be evacuated if desired via an opening 226. In a similar manner, the inner space of enclosure 22 insofar as not occupied by cell 23 and detectors 27, 28 can be evacuated, maintained under reduced pressure and/or filled with an inert gas. It is to be noted that the device illustrated herein can be said to be of the non-resonant type.

Figure 3:
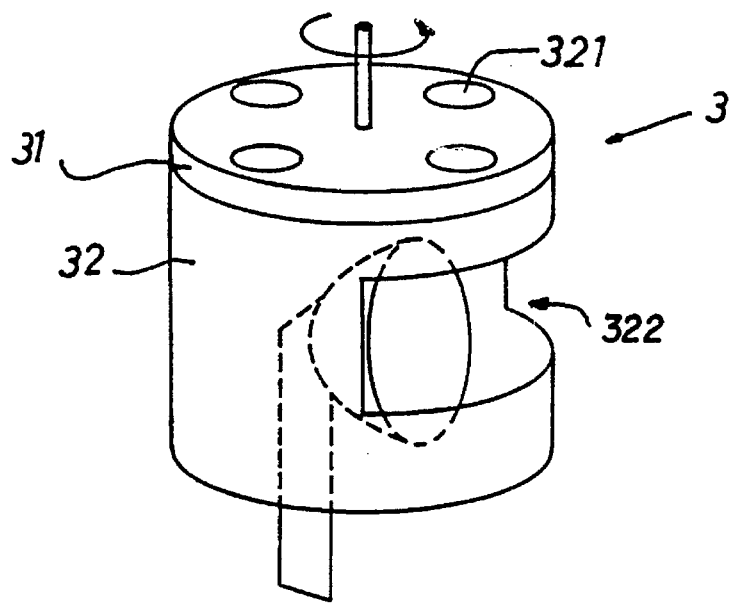
FIG. 3 is a semi-diagrammatic perspective view of a preferred embodiment of the light source for a device according to the invention.

FIG. 3 is a perspective and semi-diagrammatic view of a preferred embodiment of the pulse generator or "chopper" 3. The term "chopper" normally refers to such devices as are used on the top of emergency vehicles emitting flashes of colored light and the structure of such devices is of use in the invention. Upper wall 31 is made of a heavy disk, e.g. of stainless steel, which may have a number of equally distanced openings 321 for air cooling of the light source. Tubular side wall 32, on the other hand, should be made of a very light and thin material that is not transparent for infrared radiation, e.g. aluminum, in order to minimize the impact of imbalance caused by the absence of wall material in opening 322. Alternatively, the opening can be covered with a material that is transparent to infrared radiation and has a mass that is similar to that of an equally dimensioned segment of the material of side wall 32. It is to be noted that side edges of opening 322 can be straight as shown or rounded, depending upon the desired configuration of the light pulses.

Generally, the linear or serial arrangement of reference and measurement chambers in the cell of a device according to the invention vary in essentially the same way in dependence upon external parameters, such as temperature, impact of vibration, extraneous noise etc.

Figure 4:
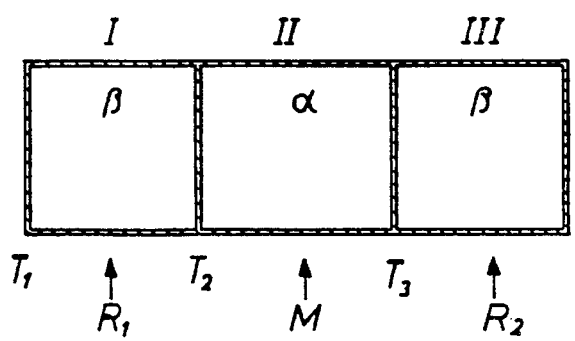
FIG. 4 is a diagram illustrating a linear or serial arrangement of two reference chambers and an intermediate measuring chamber for a photoacoustic device according to the invention.

FIG. 4 shows the diagram of a cell having three chambers, e.g. a first reference chamber I, a first measuring chamber II and an additional chamber III which could be either a reference chamber or a measuring chamber. If chamber III is a second reference cell, such arrangement permits to check the operation of the reference cells as well as the cleanliness of the entrance window of the measuring cell.

$T_1$, $T_2$, $T_3$ indicate the transmission coefficients for mathematical treatment of operation. $\alpha$ and $\beta$ indicate the absorption in the particular chamber.

Figure 5:
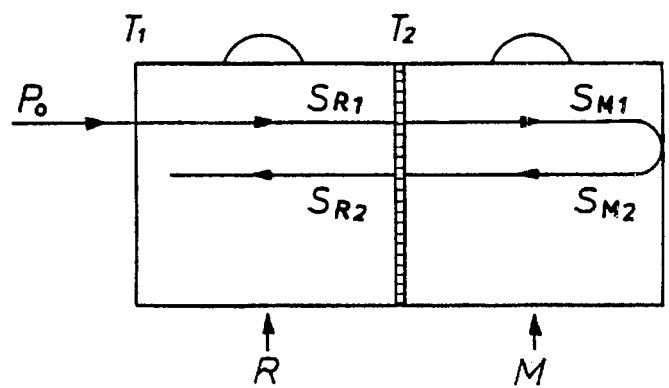
FIG. 5 is a diagrammatic illustration of the passage of the light beam when using a light-reflective layer at the end of the measuring chamber.

FIG. 5 is a diagram of a cell in which the pulses $P_0$ pass through reference chamber R as well as through measuring chamber M, and are reflected at the end of measuring chamber M by means of a mirror (not indicated in FIG. 5). Mathematical treatment of the values of reference signals $S_{R1}$, $S_{R2}$ and of measuring signals $S_{M1}$, $S_{M2}$ indicates that information about the cleanliness of the entrance window of measuring chamber M can be obtained by calculating coefficient $T_2$.

Figure 6A:
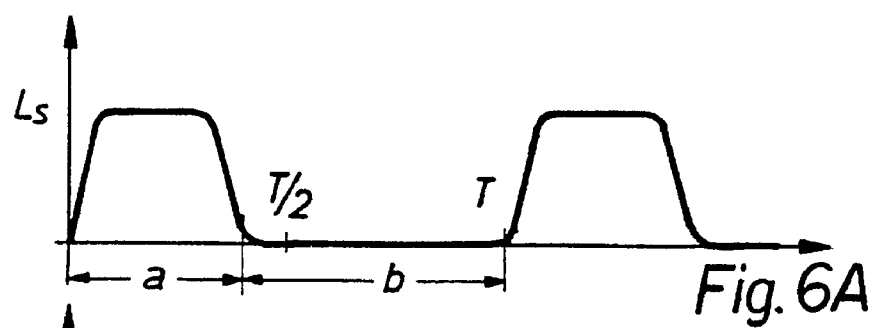
FIGS. 6 through 8 show a number of graphs for illustrating certain concepts when operating preferred embodiments of the invention.
Figure 6B:
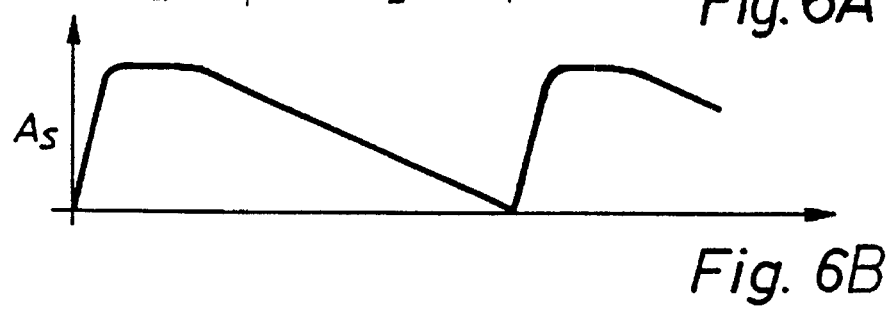

FIGS. 6A and 6B show two superimposed diagrams in which the ordinate of the upper diagram indicates the light signal $L_S$; the ordinate of the lower diagram indicates the strength of the acoustic signal $A_S$ while the abscissa of both diagrams indicates the chopper cycle T. It can be shown that the acoustic signal optimally is zero when the excitation cycle starts. Parameter a/b depends upon the frequency of modulation at <100 Hz. For example, a value for a/b of 0.44 can be obtained for a chopper window of 110°.

Figure 7:
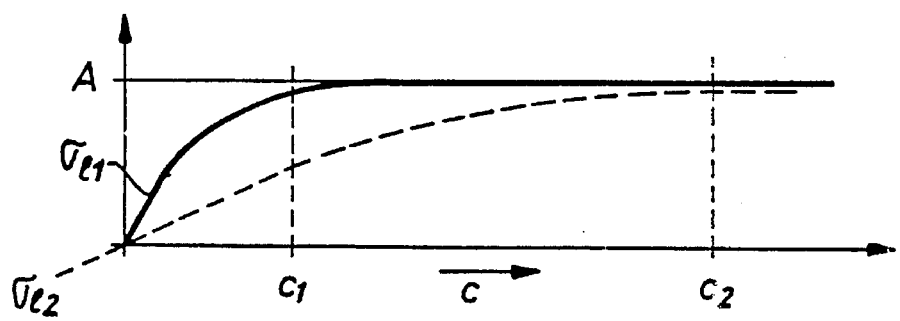

FIG. 7 shows a diagram for signal slopes $\sigma_{11}$ and $\sigma_{12}$; the ordinate indicates the strength of the acoustic signal A while the abscissa indicates the concentration c (two individual concentrations $c_1$ and $c_2$ are shown) of the species of analytical interest, e.g. ozone. Mathematical analysis indicates that if the cell length is decreased for a given acoustic signal, the measurable concentration range will increase.

Figure 9:
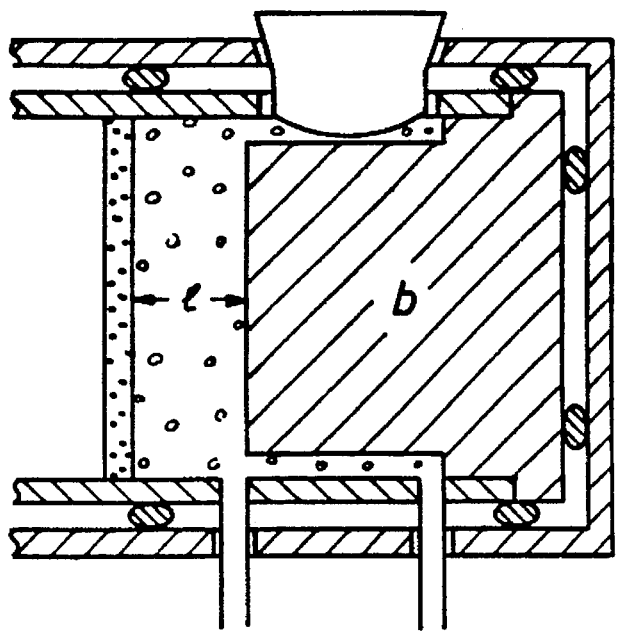
FIGS. 9 and 10 illustrate optional modifications of the measuring chamber in a device according to the invention.
Figure 10:
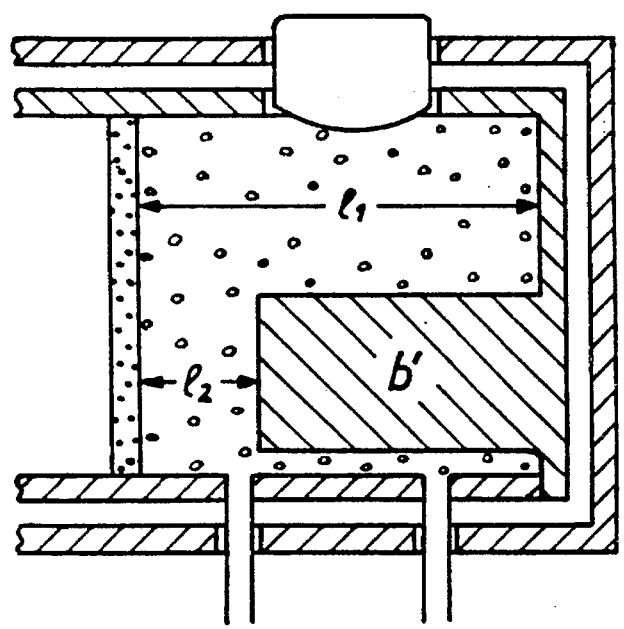

This can be applied in a measuring chamber according to the invention as illustrated in FIGS. 9 and 10, where the effective cell length "l" is decreased by insertion of a metallic stopper body b (FIG. 9) or a body b' so as to produce a measuring chamber with two differing path lengths $l_1$ and $l_2$.

Figure 8:
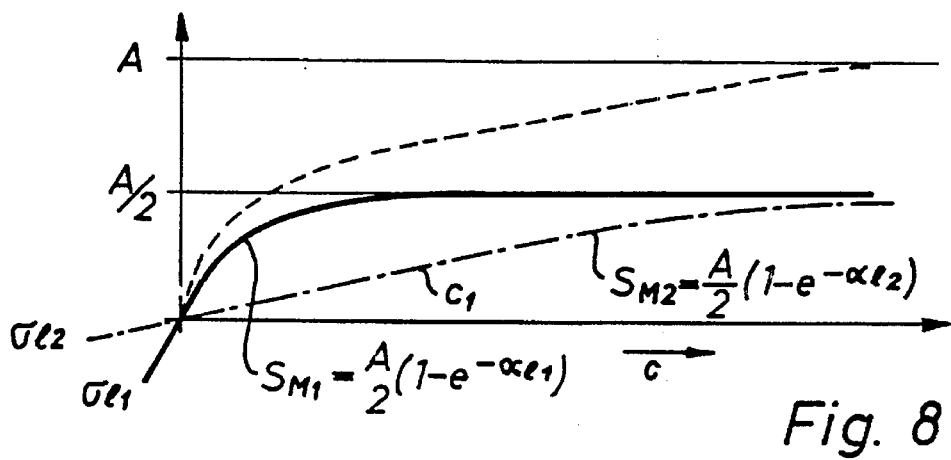

FIG. 8 is a diagram similar to that shown in FIG. 7 and indicates that maximum of detectivity (maximum detectable concentration) can be increased in this manner. For example, with l=40 mm, a detectable concentration c limit of 5% was observed for ozone whereas with l=20 mm, the detectable concentration limit was 10%. Accordingly, an insert of the type shown in FIG. 10 permits to increase the maximum of detectivity without changing the minimum of detectivity.

While the above illustrations disclose several specific embodiments of the invention, it will be apparent to those experienced in the art that many modifications and variations of the present invention are possible in the light of the above teachings and within the purview of the appended claims without departing from the spirit and intended scope of the invention.

What is claimed is:

1. A photoacoustic analyzing method comprising the steps of:

passing a pulsating beam of light having a predetermined frequency in an infrared frequency portion through an analytic device comprising at least one reference chamber containing a gaseous reference medium and at least one measuring chamber containing a gaseous analysis medium so as to cause generation of sound within said reference chamber and within said measuring chamber; said gaseous analysis medium containing an unstable chemically reactive species of interest in an unknown concentration, and said gaseous reference consisting of an inert gaseous medium having photoacoustic absorption compatible with said unstable chemically reactive species and capable of serving as a photoacoustic reference for said gaseous analysis medium; separately detecting said sound generated in said at least one reference chamber and in said at least one measuring chamber to generate a first and a second signal in relation to said sound generated in said at least one reference chamber and in said measuring chamber; and evaluating said first and said second signals in relation with said unknown concentration of said species of interest.

2. The method of claim 1 wherein said reactive chemical substance is ozone and wherein said gaseous inert medium is alkane.

3. The method of claim 1 wherein a rate of decay of said chemically reactive substance is used for calibration of the said analytic device.

4. A photoacoustic device for analysis of fluids comprising:

a source of a pulsating beam of light;

an enclosure means containing:

at least one reference chamber and at least one measuring chamber in an essentially linear arrangement in a common cell within said enclosure means;

said enclosure means and said common cell providing a path P for said pulsating beam of light through said at least one reference chamber and subsequently through said at least one measuring chamber; said at least one measuring chamber having inlet and outlet means for passing a gaseous medium containing a species of interest in an unknown concentration into and out of said at least one measuring chamber; said at least one reference chamber and said at least one measuring chamber each comprising a sound detecting means for detecting sound generated by said pulsating beam of light in said at least one reference chamber and in said at least one measuring chamber; each of said sound detecting means being capable of producing a signal in relation to said sound; and said at least one reference chamber containing a gaseous medium suitable for serving as a photoacoustic reference for said gaseous medium containing said species of interest;

wherein said cell is held in position within said enclosure by means of acoustic dampening elements.

5. A photoacoustic device for analysis of fluids comprising:

a source of a pulsating beam of light;

an enclosure means containing:

at least one reference chamber and at least one measuring chamber in an essentially linear arrangement in a common cell within said enclosure means;

said enclosure means and said common cell providing a path P for said pulsating beam of light through said at least one reference chamber and subsequently through said at least one measuring chamber; said at least one measuring chamber having inlet and outlet means for passing a gaseous medium containing a species of interest in an unknown concentration into and out of said at least one measuring chamber; said at least one reference chamber and said at least one measuring chamber comprising a sound detecting means for detecting sound generated by said pulsating beam of light in said at least one reference chamber and in said at least one measuring chamber; each of said sound detecting means being capable of producing a signal in relation to said sound; and said at least one reference chamber containing a gaseous medium suitable for serving as a photoacoustic reference for said gaseous medium containing said species of interest;

wherein said sound detecting means are in physical contact with said cell but not in physical contact with said enclosure; and wherein an acoustic shield is provided on said enclosure for protecting unwanted sound input to said sound detecting means.

* * * * *